(12) United States Patent
Nilsson

(10) Patent No.: US 6,511,996 B1
(45) Date of Patent: Jan. 28, 2003

(54) POTASSIUM SALT OF (S)-OMEPRAZOLE

(75) Inventor: Maths Nilsson, Södertälje (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/530,248

(22) PCT Filed: Jan. 18, 2000

(86) PCT No.: PCT/SE00/00087

§ 371 (c)(1),
(2), (4) Date: Apr. 26, 2000

(87) PCT Pub. No.: WO00/44744

PCT Pub. Date: Aug. 3, 2000

(30) Foreign Application Priority Data

Jan. 28, 1999 (SE) .................................. 9900274

(51) Int. Cl.⁷ .................. A61K 31/4439; C07D 401/12
(52) U.S. Cl. .................................. 514/338; 546/273.7
(58) Field of Search ........................ 514/338; 546/273.7

(56) References Cited

U.S. PATENT DOCUMENTS

| | | | |
|---|---|---|---|
| 4,738,974 A | 4/1988 | Brändström | 514/338 |
| 5,693,818 A | 12/1997 | Von Unge | 546/273.7 |
| 5,714,504 A | 2/1998 | Lindberg et al. | 514/338 |
| 5,776,765 A | 7/1998 | Graham et al. | 435/280 |
| 5,840,552 A | 11/1998 | Holt et al. | 435/118 |
| 5,877,192 A | 3/1999 | Lindberg et al. | 514/338 |
| 5,929,244 A | 7/1999 | Von Unge | 546/273.7 |
| 5,948,789 A | 9/1999 | Larsson et al. | 514/299 |
| 6,143,771 A | 11/2000 | Lindberg et al. | 514/338 |
| 6,162,816 A | 12/2000 | Bohlin et al. | 514/338 |

FOREIGN PATENT DOCUMENTS

| | | |
|---|---|---|
| EP | 0005129 | 10/1979 |
| EP | 0124495 | 1/1987 |
| EP | 0247983 | 1/1993 |
| WO | 9208716 | 5/1992 |
| WO | 9427988 | 12/1994 |
| WO | 9601623 | 1/1996 |
| WO | 9602535 | 2/1996 |
| WO | 9854171 | 12/1998 |
| WO | 98-54171 A1 * | 12/1998 |

OTHER PUBLICATIONS

CA 131:291265, Yan et al. 1999.*

* cited by examiner

*Primary Examiner*—Jane Fan
(74) *Attorney, Agent, or Firm*—White & Case LLP

(57) ABSTRACT

The present invention relates to a novel form of 5-methoxy-2-[[(4-methoxy-3,5-dimethyl-2-pyridinyl)-methyl]sulfinyl]-1H-benzimidazole, known under the generic name omeprazole. More specifically, it relates to a novel crystalline form of the potassium salt of the (S)-enantiomer of 5-methoxy-2-[[(4-methoxy-3,5-dimethyl-2-pyridinyl)methyl]sulfinyl]-1H-benzimidazole. The present invention also relates to processes for preparing such a form of the potassium salt of (S)-omeprazole and pharmaceutical compositions containing it.

9 Claims, 2 Drawing Sheets

POTASSIUM SALT OF (S)-OMEPRAZOLE

This application is a 371 of PCT/SE 00/00087 Jan. 18, 2000 now WO 00/44744.

FIELD OF THE INVENTION

The present invention relates to a novel form of 5-methoxy-2-[[(4-methoxy-3,5-dimethyl-2-pyridinyl)-methyl]sulfinyl]-1H-benzimidazole, known under the generic name omeprazole. More specifically, it relates to a novel crystalline form of the potassium salt of the (S)-enantiomer of 5-methoxy-2-[[(4-methoxy-3,5-dimethyl-2-pyridinyl)methyl]sulfinyl]-1H-benzimidazole. The present invention also relates to a process for preparing such a form of potassium salt of (S)-omeprazole and pharmaceutical compositions containing it.

BACKGROUND OF THE INVENTION AND PRIOR ART

The compound 5-methoxy-2-[[(4-methoxy-3,5-dimethyl-2-pyridinyl)methyl]sulfinyl]-1H-benzimidazole, having the generic name omeprazole, and therapeutically acceptable salts thereof, are described in EP 5129. The specific alkaline salts of omeprazole are disclosed in EP 124 495. Omeprazole is a proton pump inhibitor, i.e. effective in inhibiting gastric acid secretion, and is useful as an antiulcer agent. In a more general sense, omeprazole may be used for prevention and treatment of gastric-acid related diseases in mammals and especially in man.

Omeprazole is a sulfoxide and a chiral compound, wherein the sulfur atom is the stereogenic center. Thus, omeprazole is a racemic mixture of its two single enantiomers, the (R)- and (S)-enantiomer of omeprazole, herein referred to as (R)-omeprazole and (S)-omeprazole. The absolute configurations of the enantiomers of omeprazole have been determined by an X-ray study of an N-alkylated derivative of the (+)-enantiomer in non-salt form. The (+)-enantiomer of the non-salt form and the (−)-enantiomer of the non-salt form were found to have R and S configuration, respectively. The conditions for the optical rotation measurement for each of these enantiomers are described in WO 94/27988.

Certain salts of the single enantiomers of omeprazole and their preparation are disclosed in WO 94/27988. These compounds have improved pharmacokinetic and metabolic properties which will give an improved therapeutic profile such as a lower degree of interindividual variation.

WO 96/02535 discloses a process for the preparation of the single enantiomers of omeprazole and structually related compounds as well as salts thereof WO 96/01623 discloses pharmaceutical dosage forms comprising for instance magnesium salts of (R)-and (S)-omeprazole.

WO 98/54171 discloses a process for the preparation of the trihydrate of magnesium salt of (S)-omeprazole, wherein the potassium salt of (S)-omeprazole is used as an intermediate. The potassium salt of (S)-omeprazole, according to the prior art, crystallizes as a methanol solvate.

Certain salts of of (S)-omeprazole, such as the potassium salt, are in general suitable compounds for i.v.-administration due to their intrinsic properties, such as high stability and high solubility in water. Methanol solvates are however not suitable for i.v.-administration, since the concomitant administration of methanol could be fatal for the receiver. Therefore there exists a need for a potassium salt of (S)-omeprazol that is free from methanol.

The novel form of the potassium salt of (S)-omeprazole according to the present invention is hereinafter referred to as the potassium salt of (S)-omeprazole form B. The prior art form of the potassium salt of (S)-omeprazole disclosed in WO 98/54171 is hereinafter referred to as the potassium salt of (S)-omeprazole form A.

DESCRIPTION OF THE INVENTION

Figure 1:
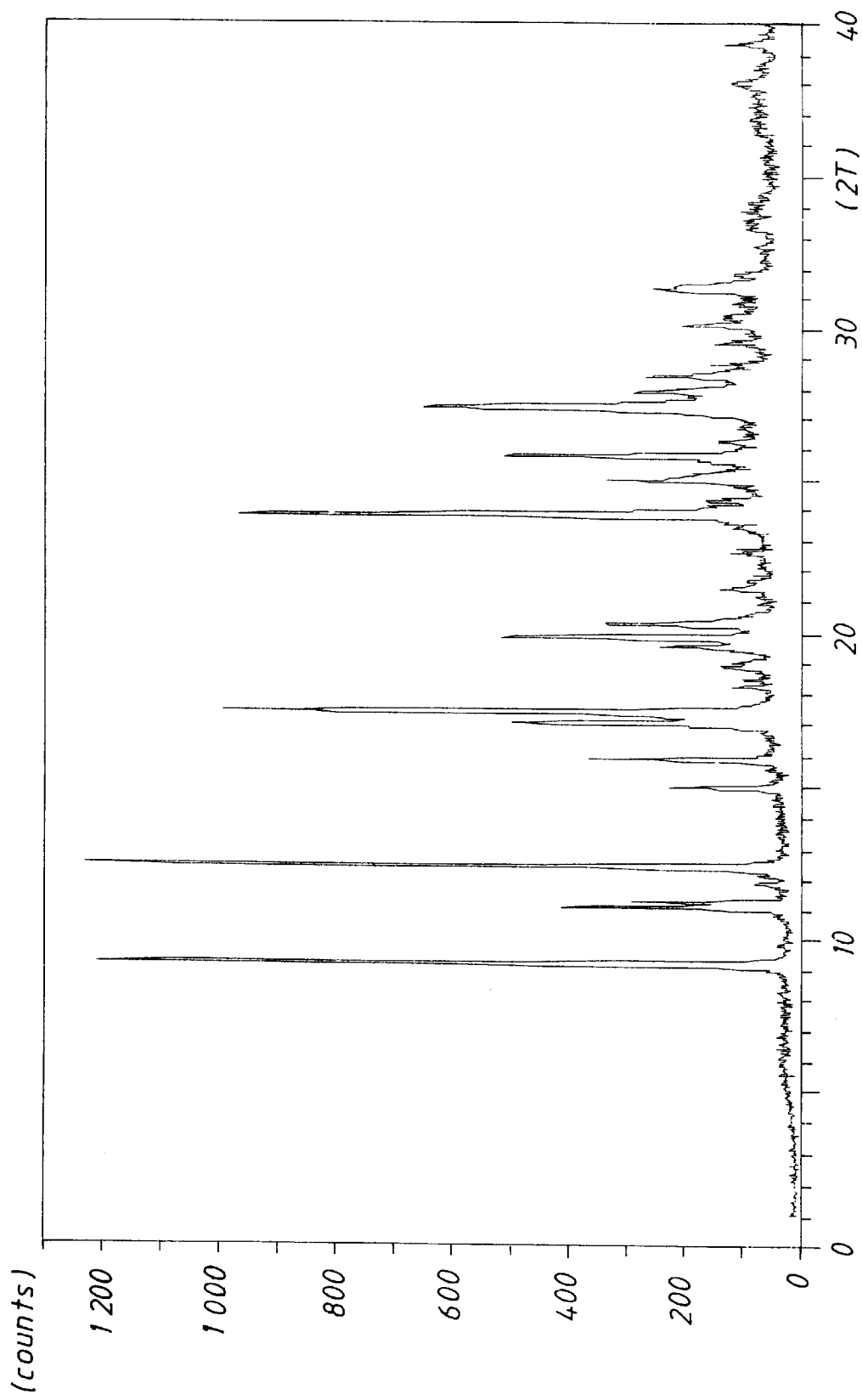
FIG. 1 is an X-ray powder diffractogram of the potassium salt of (S)-omeprazole prepared according to the present invention, i.e. form B.
Figure 2:
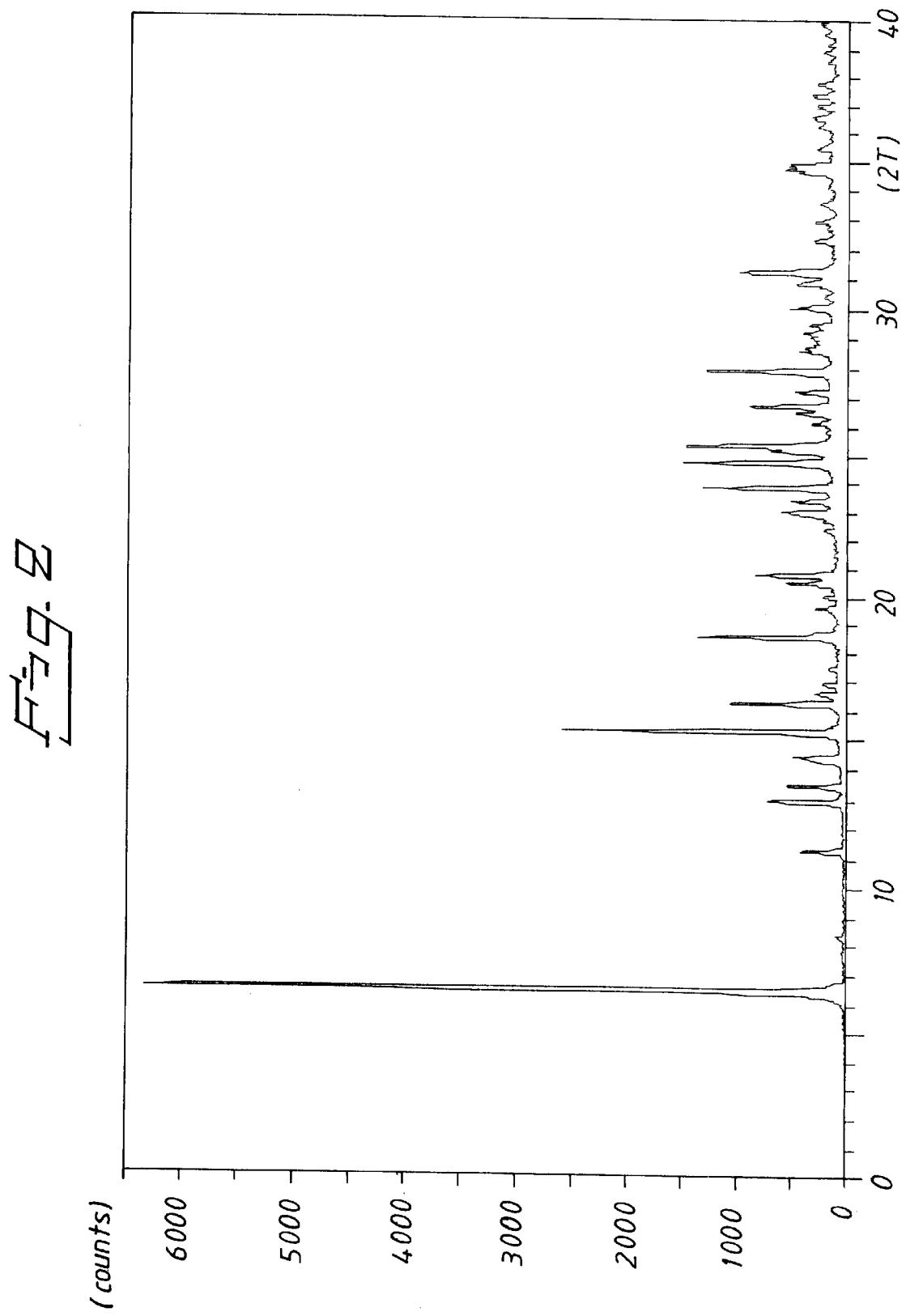
FIG. 2 is an X-ray powder diffractogram of the potassium salt of (S)-omeprazole prepared according to example 2 in WO 98/54171, i.e. form A.

It has surprisingly been found that the potassium salt of (S)-omeprazole occurs in a number of structurally different forms. It is an object of the present invention to provide a substantially pure potassium salt of (S)-omeprazole form B.

The potassium salt of (S)-omeprazole form B is advantageous because it is hydrate form, is while the previous known form A is methanol solvate. The potassium salt of (S)-omeprazole form B is especially suitable for intravenous administration. The potassium salt of (S)-omeprazole form B is further characterized by being crystalline, and preferably being highly crystalline.

The potassium salt of (S)-omeprazole form B, obtained according to the present invention, is substantially free from other forms of potassium salts of (S)-omeprazole, such as the corresponding form A described in the prior art The potassium salt of (S)-omeprazole form B obtained according to the present invention is also substantially free from potassium salts of (R)-omeprazole.

The potassium salt of (S)-omeprazole form B is characterized by the positions and intensities of the major peaks in the X-ray powder diffractogram, but may also be characterized by conventional FT-IR spectroscopy. These characteristics are not exhibited by any other forms of potassium salt of (S)-omeprazole and accordingly, the potassium salt of (S)-omeprazole form B is easily distinguishable from any other crystal forms of potassium salts of (S)-omeprazole disclosed in prior art. With the expression "any form" is meant anhydrates, hydrates, solvates, amorphous forms, and polymorphs. Such examples of any forms of potassium salt of (S)-omeprazole includes, but are not limited to, anhydrates, monohydrates, dihydrates, sesquihydrates, trihydrates, alcoholates, such as methanolates and ethanolates, amorphous forms and polymorphs.

The potassium salt of (S)-omeprazole form B may also be characterized by its unit cell.

In a further aspect, the present invention provides a process for the preparation of the potassium salt of (S)-omeprazole form B which comprises the step of converting (S)-omeprazole into the corresponding potassium salt in toluene or dichloromethane by treatment with a potassium source, such as potassium hydroxide or potassium methylate, followed by isolation of the formed salt.

The crude (S)-omeprazole used in the process can for example be prepared by oxidizing 5-methoxy-2-[[(4-methoxy-3,5-dimethyl-2-pyridinyl)methyl]thio]-1H-benzimidazole into (S)-omeprazole, with an oxidizing agent and a chiral titanium complex, optionally in the presence of a base in an organic solvent, such as toluene or dichloromethane, as is described in the prior art, see WO 98/54171.

The potassium salt of (S)-omeprazole form B, prepared according to the present invention is analyzed, characterized and differentiated from the previous known form A by X-ray powder diffraction, a technique which is known per se. Another suitable technique to analyze, characterize and differentiate the potassium salt of (S)-omeprazole form B from the corresponding form A is by conventional FT-IR.

The amount of water in the potassium salt of (S)-omeprazole form B is determined by thermogravimetric analysis (TGA), a technique which is known per se.

The potassium salt of (S)-omeprazole form B is effective as a gastric acid secretion inhibitor, and is useful as an antiulcer agent. In a more general sense, it can be used for treatment of gastric-acid related conditions in mammals and especially in man, including e.g. reflux esophagitis, gastritis, duodenitis, gastric ulcer and duodenal ulcer. Furthermore, it may be used for treatment of other gastrointestinal disorders where gastric acid inhibitory effect is desirable e.g. in patients on non-steroidal anti-inflammatory drug (NSAID) therapy, in patients with Non Ulcer Dyspepsia, in patients with symptomatic gastro-esophageal reflux disease, and in patients with gastrinomas. The potassium salt of (S)-omeprazole form B may also be used in patients in intensive care situations, in patients with acute upper gastrointestinal bleeding, pre- and postoperatively to prevent aspiration of gastric acid and to treat stress ulceration. Further, the potassium salt of (S)-omeprazole form B may be useful in the treatment of psoriasis as well as in the treatment of Helicobacter infections and diseases related to these. The potassium salt of (S)-omeprazole form B may also be used for treatment of inflammatory conditions in mammals, including man.

Any suitable route of administration may be employed for providing the patient with an effective dosage of the potassium salt of (S)-omeprazole form B, according to the present invention. For example, peroral or parenteral formulations and the like may be employed. Dosage forms include capsules, tablets, dispersions, suspensions and the like. The potassium salt of (S)-omeprazole form B is, because of being highly soluble in water, especially suitable for parenteral formulations, such as i.v.

According to the invention there is further provided a pharmaceutical composition comprising the potassium salt of (S)-omeprazole form B, as active ingredient, in association with a pharmaceutically acceptable carrier, diluent or excipient and optionally other therapeutic ingredients. Compositions comprising other therapeutic ingredients are especially of interest in the treatment of Helicobacter infections. The invention also provides the use of the potassium salt of (S)-omeprazole form B in the manufacture of a medicament for use in the treatment of a gastric-acid related condition and a method of treating a gastric-acid related condition which method comprises administering to a subject suffering from said condition a therapeutically effective amount of the potassium salt of (S)-omeprazole form B.

The compositions of the invention include compositions suitable for peroral or parenteral administration. The compositions may be conveniently presented in unit dosage forms, and prepared by any methods known in the art of pharmacy.

In the practice of the invention, the most suitable route of administration as well as the magnitude of a therapeutic dose of the potassium salt of (S)-omeprazole form B in any given case will depend on the nature and severity of the disease to be treated. The dose, and dose frequency, may also vary according to the age, body weight, and response of the individual patient. Special requirements may be needed for patients having Zollinger-Ellison syndrome, such as a need for higher doses than the average patient. Children and patients with liver diseases as well as patients under long term treatment will generally benefit from doses that are somewhat lower than the average. Thus, in some conditions it may be necessary to use doses outside the ranges stated below. Such higher and lower doses are within the scope of the present invention.

In general, a suitable dosage form may cover a dose range from 5 mg to 120 mg total daily dose, administered in one single dose or equally divided doses. A preferred dosage range is from 5 mg to 100 mg, and more preferred 10 mg to 80 mg. A suitable administration dose is 20 mg to 40 mg for intravenous administration as well as oral administration The compound of the invention may be combined as the active component in intimate admixture with a pharmaceutical carrier according to conventional techniques. Especially suitable oral formulations are described in WO 96/01623 and EP 247 983, the disclosures of which are hereby incorporated as a whole by reference.

Combination therapies comprising the potassium salt of (S)-omeprazole form B and other active ingredients in separate dosage forms may also be used. Examples of such active ingredients include anti-bacterial compounds, non-steroidal anti-inflammatory agents, antacid agents, alginates and prokinetic agents.

The examples which follow will further illustrate the preparation of the compound of the invention, i.e. the potassium salt of (S)-omeprazole form B, but are not intended to limit the scope of the invention as defined hereinabove or as claimed below.

EXAMPLES

Potassium Salt of (S)-omeprazole Form B

A solution of 5-methoxy-2-[[(4-methoxy-3,5-dimethyl-2-pyridinyl)methyl]thio]-1H-benzimidazole (67 mmol) in toluene (4 mL/g 5-methoxy-2-[[(4-methoxy-3,5-dimethyl-2-pyridinyl)methyl]thio]-1H-benzimidazole) was charged with water (0,9 mmol) and D-(−)-diethyl tartrate (14 mmol) at 50° C. After stirring for 20 minutes, titanium(IV) isopropoxide (6,5 mmol) was added and the solution was stirred for approximately 50 minutes. The reaction mixture was temperated to 35° C. and N,N-diisopropylethylamine (10 mmol) was added. Cumene hydroperoxide (74 mmol) was then charged to the solution while keeping the temperature at approximately 35° C.

After 3 hours, the reaction mixture was diluted with toluene (2 m lL/g 5-methoxy-2-[[(4-methoxy-3,5-dimethyl-2-pyridinyl)methyl]thio]-1H-benzimidazole) and potassium methoxide (26 mmol) was added as a slurry in toluene (8 mL/g KOMe). The obtained crystals were filtered off and dried (36° C., vacuum) over night. Yield 0,72 g (1,9 mmol; 7 % in respect of KOMe).

Content of solvents as obtained with Karl-Fischer titration and GC respectively (% w/w)

Water 3,4

Methanol 0,01

TGA

Approximately 2 % (w/w) of the water content is incorporated in the crystal lattice (i.e. ~0,5 $H_2O$/ molecule of potassium salt of (S)-omeprazole form B)

XRD

The X-ray powder diffractogram of the product measured from 1–40° in 2θ with CuKα$_1$ radiation shows the following characteristic list of peaks:

| d-value [Å] | Intensity |
|---|---|
| 9.6 | very strong |
| 8.0 | strong |
| 7.9 | strong |
| 7.5 | weak |
| 7.3 | weak |
| 7.2 | very strong |
| 5.9 | strong |
| 5.6 | strong |
| 5.2 | strong |
| 5.1 | very strong |
| 4.88 | weak |
| 4.83 | weak |
| 4.71 | weak |
| 4.67 | weak |
| 4.55 | medium |
| 4.49 | strong |
| 4.39 | strong |
| 4.15 | weak |
| 4.10 | weak |
| 3.95 | weak |
| 3.74 | very strong |
| 3.67 | medium |
| 3.58 | strong |
| 3.55 | medium |
| 3.47 | strong |
| 3.40 | weak |
| 3.27 | strong |
| 3.20 | medium |
| 3.15 | medium |
| 3.10 | weak |
| 3.03 | weak |
| 2.98 | medium |
| 2.87 | medium |
| 2.85 | medium |
| 2.38 | medium |
| 2.30 | weak |

In addition the diffractogram contains several weak peaks that have been omitted for clarity.

The peaks, identified with d-values calculated from the Bragg formula and intensities, have been extracted from the diffractogram of the potassium salt of (S)-omeprazole form B. The relative intensities are less reliable and instead of numerical values the following definitions are used;

| % Relative Intensity | Definition |
|---|---|
| 25–100 | vs (very strong) |
| 10–25 | s (strong) |
| 3–10 | m (medium) |
| 1–3 | w (weak) |

What is claimed is:

1. The potassium salt of (S)-omeprazole form B, wherein the compound is in a hydrate form and provides an X-ray powder diffraction pattern exhibiting substantially the following d-values:

| d-value [Å] | Intensity |
|---|---|
| 9.6 | very strong |
| 8.0 | Strong |
| 7.9 | Strong |
| 7.5 | Weak |
| 7.3 | Weak |
| 7.2 | very strong |
| 5.9 | Strong |
| 5.6 | Strong |
| 5.2 | Strong |
| 5.1 | very strong |
| 4.88 | Weak |
| 4.83 | Weak |
| 4.71 | Weak |
| 4.67 | Weak |
| 4.55 | medium |
| 4.49 | Strong |
| 4.39 | Strong |
| 4.15 | Weak |
| 4.10 | Weak |
| 3.95 | Weak |
| 3.74 | very strong |
| 3.67 | Medium |
| 3.58 | Strong |
| 3.55 | Medium |
| 3.47 | Strong |
| 3.40 | Weak |
| 3.27 | Strong |
| 3.20 | Medium |
| 3.15 | Medium |
| 3.10 | Weak |
| 3.03 | Weak |
| 2.98 | Medium |
| 2.87 | Medium |
| 2.85 | Medium |
| 2.38 | Medium |
| 2.30 | Weak. |

2. The potassium salt of (S)-omeprazole form B according to claim 1, wherein the compound is in a crystalline form.

3. A process for the preparation of potassium salt of (S)-omeprazole form B as claimed in claim 1 or 2, which comprises the step of converting (S)-omeprazole into the corresponding potassium salt in toluene or dichloromethane by treatment with a potassium source, followed by isolation of the formed salt, wherein a substantially methanol-free system is used.

4. A process according to claim 3, wherein (S)-omeprazole is obtained by oxidizing 5-methoxy-2-[[(4-methoxy-3,5-dimethyl-2-pyridinyl)methyl]thio]-1H-benzimidazole, with an oxidizing agent and a chiral titanium complex, optionally in the presence of a base in an organic solvent.

5. A pharmaceutical formulation comprising the potassium salt of (S)-omeprazole form B as claimed in claim 1 or 2 in admixture with a pharmaceutically acceptable excipient.

6. A pharmaceutical formulation comprising a therapeutically effective a mount of the potassium salt of (S)-omeprazole form B as claimed in claim 1 or 2 in admixture with a pharmaceutically acceptable excipient.

7. A method for inhibiting gastric acid secretion which comprises administration of a therapeutically effective amount of the potassium salt of (S)-omeprazole form B as claimed in claim 1 or 2 to a patient in need of such inhibition.

8. A method for the treatment of gastrointestinal inflammatory diseases which comprises administering a therapeutically effective amount of the potassium salt of (S)-omeprazole form B as claimed in claim 1 or 2 to a patient in need of such treatment.

9. A method for the treatment of conditions involving infection by *Helicobacter pylori* of human gastric mucosa, which comprises administering a therapeutically effective amount of the potassium salt of (S)-omeprazole as claimed in claim 1 or 2 to a patient in need of such treatment.

* * * * *